US009873712B2

(12) United States Patent
Meng et al.

(10) Patent No.: US 9,873,712 B2
(45) Date of Patent: Jan. 23, 2018

(54) METHOD OF PURIFYING IDRAPARINUX SODIUM

(71) Applicant: AMPHASTAR PHARMACEUTICALS INC., Rancho Cucamonga, CA (US)

(72) Inventors: Jundong Meng, Nanjing (CN); Yonggang Xu, Nanjing (CN); Wencun Wang, Nanjing (CN); Song Chen, Nanjing (CN); Haoning Zhang, Nanjing (CN)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/714,191

(22) Filed: May 15, 2015

(65) Prior Publication Data

US 2016/0096856 A1    Apr. 7, 2016

Related U.S. Application Data

(60) Provisional application No. 62/059,793, filed on Oct. 3, 2014.

(51) Int. Cl.
*C07H 1/06* (2006.01)
*C07H 15/04* (2006.01)

(52) U.S. Cl.
CPC ............ *C07H 1/06* (2013.01); *C07H 15/04* (2013.01)

(58) Field of Classification Search
CPC ............ C07H 15/04; C07H 3/00; C07H 1/06
USPC ........................................... 536/18.2
See application file for complete search history.

(56) References Cited

U.S. PATENT DOCUMENTS

| 6,174,863 | B1 | 1/2001 | van Boeckel et al. |
| 2011/0105418 | A1* | 5/2011 | Nadji ............ A61K 31/737 514/25 |
| 2012/0041189 | A1 | 2/2012 | Clavel et al. |
| 2012/0108544 | A1 | 5/2012 | Mourier et al. |

FOREIGN PATENT DOCUMENTS

| EP | 0 454 220 A1 | 10/1991 |
| EP | 0454220 A1 | 10/1991 |

OTHER PUBLICATIONS

Bio-Rad LIT203 Rev B: AG® 50W and AG MP-50 Cation Exchange Resins Instruction Manual. Jun. 17, 1998. http://www.manualsdir.com/manuals/600443/bio-rad-agmp-50-cation-exchange-resins-ag-50w-cation-exchangeresins-analytical-grade-cation-exchange-resin.html?page=13cation-exchange-resins-analytical-grade-cationexchange-resin.html?page=13.*
GE Data File 28-9137-87 AC: Sephadex™ G-25 media and prepacked formats. First published Apr. 2007.*
Driguez et al. Synthetic oligosaccharides as active pharmaceutical ingredients: Lessons learned from the full synthesis of one heparin derivative on a large scale. Nat. Prod. Rep., 31:980-989, 2014, first published Apr. 7, 2014.*
PCT/US2015/053350 International Search Report and Written Opinion, dated Jan. 29, 2016, 11 pages.
Herczeg, et al., Novel syntheses of Idraparinux, the anticoagulant pentasaccharide with indirect selective factor Xa inhibitory activity, Elsevier, Tetrahedron, vol. 69, 2013, pp. 3149-3158.
Chen, Chen, et al., "Efficient synthesis of Idraparinux, the anticoagulant pentasaccharide," Bioorganic & Medicinal Chemistry Letters, 19, 2009, pp. 3875-3879.
Herczeg, Mihály, et al., "Novel syntheses of Idraparinux, the anticoagulant pentasaccharide with indirect selective factor Xa inhibitory activity," Tetrahedron, 69, 2013, pp. 3149-3158.
https://en.wikipedia.org/wiki/Factor_X, 12 pages, accessed in 2015.
https://en.wikipedia.org/wiki/Indraparinux, 2 pages, accessed in 2015.

* cited by examiner

*Primary Examiner* — Yih-Horng Shiao
(74) *Attorney, Agent, or Firm* — Lewis Roca Rothgerber Christie LLP

(57) ABSTRACT

A method for the purification of idraparinux sodium includes: passing a solution including a crude idraparinux sodium through a column including a sodium ion exchange resin to obtain a first mixture; passing a solution including the first mixture through a gel chromatogaphy column to obtain a second mixture; and precipitating a purified idraparinux sodium from a solution including the second mixture.

25 Claims, 4 Drawing Sheets

METHOD OF PURIFYING IDRAPARINUX SODIUM

CROSS-REFERENCE TO RELATED APPLICATION

This application claims priority to and the benefit of related U.S. Provisional Application Ser. No. 62/059,793, filed in the U.S. Patent and Trademark Office on Oct. 3, 2014, the entire content of which is incorporated herein by reference.

BACKGROUND

1. Field

The following description is related to a process for the purification of idraparinux sodium, i.e., nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-idopyranuronosyl-(1→4)-2,3,6-tri-O-sulfonato-α-D-glucopyranoside.

2. Background

Idraparinux sodium is an anticoagulant medication chemically related to low molecular weight heparins. Idraparinux sodium is a synthetic pentasaccharide Factor Xa inhibitor and has been used as an anticoagulant and antithrombotic medication. One feature of idraparinux sodium over low-molecular-weight heparin (LMWH) or unfractionated heparin is that the risk for heparin-induced thrombocytopenia (HIT) may be substantially lower for treatments utilizing idraparinux sodium.

Idraparinux sodium has a chemical structure similar to, and a method of action substantially the same as, fondaparinux, an LMWH. However, idraparinux sodium has an elimination half-life of about five to about six times longer than fondaparinux (e.g., the half-life of idraparinux sodium is approximately 80 hours while that of fondaparinux is about 17 hours). Because of the long half-life, idraparinux sodium may be injected into a patient only once per week.

The structure of idraparinux sodium may be illustrated as follows:

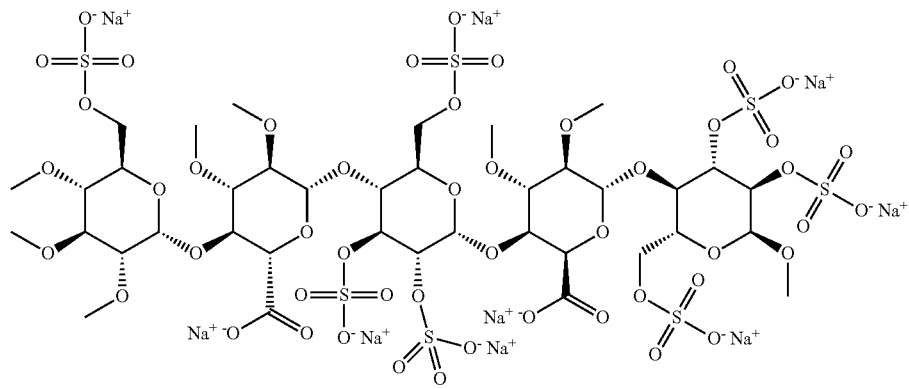

Idraparinux sodium may be synthesized via a [4+1] strategy as disclosed in U.S. Pat. No. 6,174,863 B1 and EP0454220B1, or via a [3+2] strategy as disclosed by Herczeg (Herczeg Mihály, "Novel Syntheses of Idraparinux, the Anticoagulant Pentasaccharide with Indirect Selective Factor Xa Inhibitory Activity", *Tetrahedron*, 2013, 69(15): 3149-3158) and Yu (Yu B. and Chen C., "Efficient Synthesis of Idraparinux, the anticoagulant pentasaccharide", *Bioorganic & Medicinal Chemistry Letters*, 2009, 19(14): 3875-3879).

The idraparinux sodium synthesized according to the above-identified methods contains impurities, such as organic impurities (e.g., carboxyl group containing and sulfonic group containing salts, such as disaccharide and trisaccharide isomers, triethylamine salt, etc.), and inorganic impurities (e.g., sodium acetate, sulfate salt, etc.).

The purity of the synthesized idraparinux sodium (i.e., the crude idraparinux sodium) obtained utilizing these methods is only about 60% to about 70%, which does not meet certain requirements for active pharmaceutical ingredients (API) for the pharmaceutical industry (i.e., an API purity of about 99%).

SUMMARY

Aspects of embodiments of the present disclosure generally relate to a method for purification of idraparinux sodium to remove impurities present or generated during the chemical synthesis of idraparinux sodium. The purity of idraparinux sodium prepared according to embodiments of the purification process may be improved from 60-70% in the crude idraparinux sodium to at least 99.0% (e.g., greater than 99.0%), for example, 99.5% or greater, where the % of idraparinux sodium is calculated from the peak area of the idraparinux sodium measured by high performance liquid chromatography.

According to embodiments of the present disclosure, a method for obtaining at least 99.0% pure idraparinux sodium including nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-dopyranuronosyl-(1→4)-2,3,6-tri-O-sulfonato-α-D-glucopyranoside) includes: passing a solution including a crude idraparinux sodium through a column including a sodium ion exchange resin to obtain a first mixture; passing a solution including the first mixture through a gel chromatography column to obtain a second mixture; and precipitating a purified idraparinux sodium from a solution including the second mixture. The precipitating of the purified idraparinux sodium from the solution including second mixture may be performed utilizing a first solvent.

The first solvent utilized for the precipitating of the purified idraparinux sodium may include an alcohol, a ketone, acetonitrile, or a mixture thereof.

The first solvent may include an alcohol selected from methanol, ethanol, propanol, ethanediol, 1,2-propanediol, 1,3-propanediol, glycerine, and mixtures thereof.

The first solvent may include a ketone selected from acetone, butanone, and mixtures thereof.

The passing of the solution including the crude idraparinux sodium through the column including the sodium ion exchange resin may include: dissolving the crude idraparinux sodium in a second solvent to obtain the solution including the crude idraparinux sodium; passing the solution including the crude idraparinux sodium through the column including the sodium ion exchange resin; and collecting and concentrating an eluent of the column including the sodium ion exchange resin to obtain the first mixture.

The second solvent may include water.

The concentration of the crude idraparinux sodium in the second solvent may be about 0.1 to about 2.0 g/ml.

The method may further include washing the column including the sodium ion exchange resin with a third solvent during the collecting of the eluent.

The third solvent may include water.

The mesh number of the column including the sodium ion exchange resin may be 100 mesh to 200 mesh.

The gel chromatography column may include a beaded gel filtration medium prepared by cross-linking dextran with epichlorohydrin under alkaline conditions.

The passing of the solution including the first mixture through the gel chromatography column may include: dissolving the first mixture in a fourth solvent to obtain the solution including the first mixture; passing the solution including the first mixture through the gel chromatography column; and collecting and concentrating an eluent of the gel chromatography column to obtain the second mixture.

The fourth solvent may include a mixture of the first solvent and water. For example, the fourth solvent may include a methanol-water mixture. The amount of the first solvent in the fourth solvent may be 0 v/v % to 10 v/v % (e.g., greater than 0 v/v % to 10 v/v %, or 2 v/v % to 10 v/v %) based on a total volume of the fourth solvent. For example, the amount of the first solvent in the fourth solvent may be 4 v/v % to 6 v/v % based on a total volume of the fourth solvent.

The concentration of the first mixture in the solution including the first mixture may be about 0.1 to about 2.0 g/ml.

The passing of the solution including the first mixture through the gel chromatography column may be conducted a plurality of times utilizing the collected eluent.

The method may further include washing the column including the gel chromatography with the fourth solvent during the collecting of the eluent.

The fourth solvent may include a mixture of the first solvent and water. For example, the fourth solvent may include a methanol-water mixture. The amount of the first solvent in the fourth solvent may be 0 v/v % to 10 v/v % (e.g., greater than 0 v/v % to 10 v/v %, or 2 v/v % to 10 v/v %) based on a total volume of the fourth solvent. For example, the amount of the first solvent in the fourth solvent may be 4 v/v % to 6 v/v % based on a total volume of the fourth solvent The first solvent utilized for the precipitating of the purified idraparinux sodium may include an alcohol, a ketone, acetonitrile, or a mixture thereof.

The first solvent may include an alcohol selected from methanol, ethanol, propanol, ethanediol, 1,2-propanediol, 1,3-propanediol, glycerine, and mixtures thereof.

The first solvent may include a ketone selected from acetone, butanone, and mixtures thereof.

The precipitating of the purified idraparinux sodium from the solution including the second mixture may include: dissolving the second mixture in a fifth solvent to obtain the solution including the second mixture; adding the first solvent into the solution including the second mixture to obtain a mixed solution; cooling the mixed solution to precipitate the purified idraparinux sodium, and filtering and collecting the purified idraparinux sodium.

The concentration of the second mixture in the solution including the second mixture may be about 0.1 to about 2.0 g/ml. The dissolving of the second mixture in the fifth solvent may be conducted at a temperature of about 30° C. to about 50° C. The mixed solution may be cooled to a temperature of about −30° C. to about 15° C. (e.g., about 10° C. to about 15° C.).

A ratio of a volume of the first solvent to a volume of the fifth solvent may be about 1:1 to about 12:1, for example, about 2:1 to about 6:1.

The fifth solvent may include water.

According to embodiments of the present disclosure, a method for obtaining at least 99.0% pure idraparinux sodium including nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-dopyranuronosyl-(1→4)-2,3,6-tri-O-sulfonato-α-D-glucopyranoside) includes: passing a solution including a crude idraparinux sodium through a gel chromatography column to obtain a first mixture; passing a solution including the first mixture through a column including a sodium ion exchange resin to obtain a second mixture; and precipitating a purified idraparinux sodium from a solution including the second mixture.

BRIEF DESCRIPTION OF THE DRAWINGS

These and/or other aspects will become apparent and more readily appreciated from the following description, taken in conjunction with the accompanying drawings in which.

DETAILED DESCRIPTION

The following detailed description is provided only for purposes of illustration of embodiments of the present disclosure and not for purposes of limiting the scope of the present invention. Alternate embodiments will be readily apparent to those of skill in the art and are intended to be included within the scope of the present invention. Expressions such as "at least one of," when preceding a list of elements, modify the entire list of elements and do not modify the individual elements of the list. Further, the use of "may" when describing embodiments of the present disclosure refers to "one or more embodiments of the present disclosure."

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. §112, first paragraph, and 35 U.S.C. §132(a).

Embodiments of the present disclosure are directed toward purifying crude idraparinux sodium by way of sodium ion exchange chromatography and gel chromatography. According to aspects of embodiments of the present disclosure, the purification method is not complex, the resulting purity is at least 99.0% (or greater than 99.0%), and the method is suitable for industrialization. Throughout the present disclosure, references to "%" of a compound indicate a peak area (area %) of the compound relative to the total peak area as measured by high performance liquid chromatography (HPLC) for a sample including the compound, unless the context clearly indicates otherwise. For example, a sample including at least 99.0% pure idraparinux sodium may provide a peak area of at least 99.0% relative to the total peak area of the sample including the idraparinux sodium, as measured by HPLC.

Figure 1:
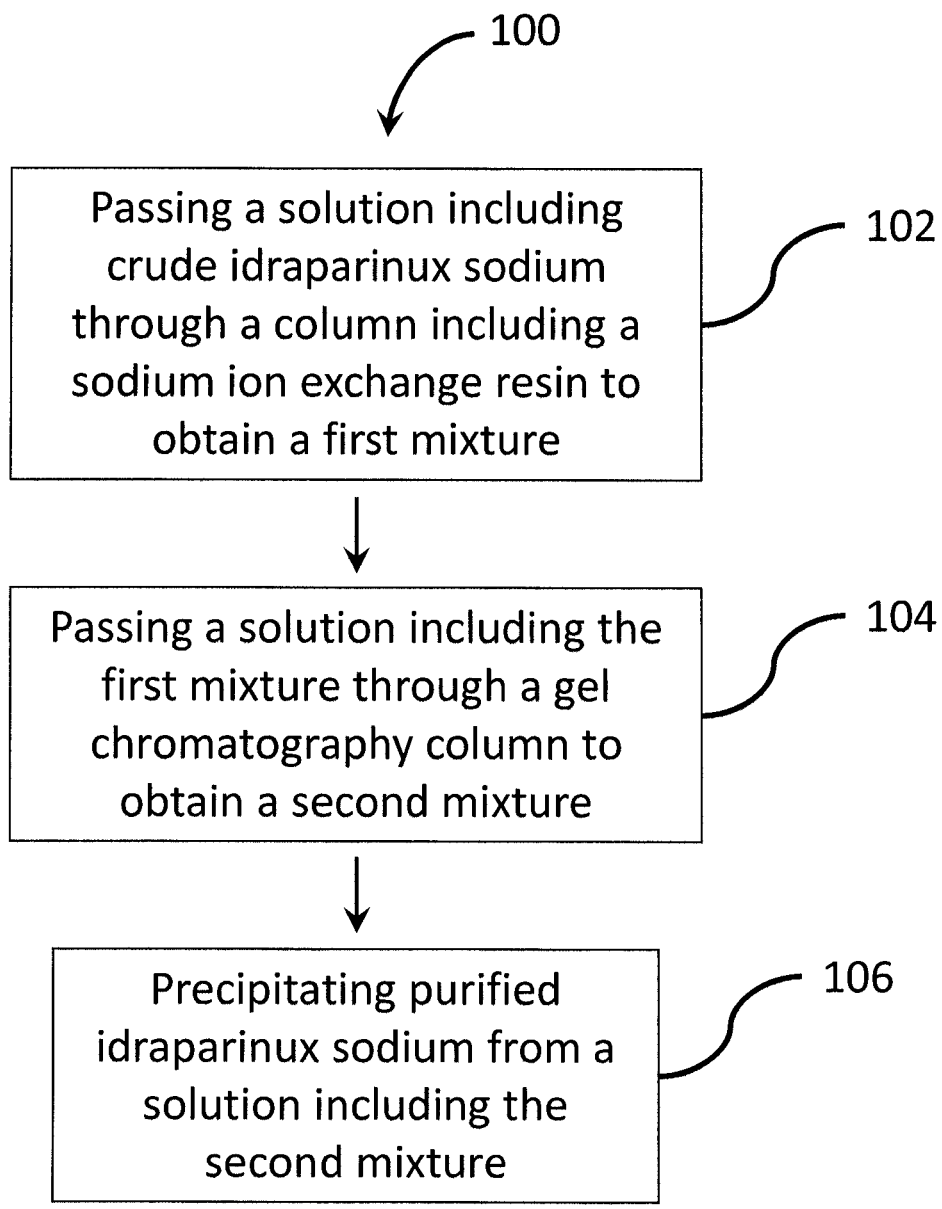
FIG. 1 is a flow chart showing a method for obtaining at least 99.0% pure idraparinux sodium according to an embodiment of the present disclosure.

FIG. 1 is a flow chart showing a method for obtaining at least 99.0% pure idraparinux sodium according to an embodiment of the present disclosure. Referring to FIG. 1, a method 100 for obtaining at least 99.0% pure idraparinux sodium (i.e., nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-dopyranuronosyl-(1→4)-2,3,6-tri-O-sulfonato-α-D-glucopyranoside) includes: 102 passing a solution including crude idraparinux sodium through a column including a sodium ion exchange resin to obtain a first mixture; 104 passing a solution including the first mixture through a gel chromatography column to obtain a second mixture; and 106 precipitating purified idraparinux sodium from a solution including the second mixture. The first mixture and the second mixture each include idraparinux sodium. The purified idraparinux sodium may be precipitated from the solution including the second mixture by utilizing a first solvent.

The present disclosure is not limited to the order in which the active acts are presented. For example, although FIG. 1 shows 102 passing the solution including crude idraparinux sodium through the column including a sodium ion exchange resin to obtain the first mixture followed by 104 passing the solution including the first mixture through the gel chromatography column to obtain the second mixture, the order of those acts may be switched. In some embodiments of the disclosure, a method for obtaining at least 99.0% pure idraparinux sodium includes: passing a solution including crude idraparinux sodium through a gel chromatography column to obtain a first mixture; passing a solution including the first mixture through a column including a sodium ion exchange resin to obtain a second mixture; and precipitating purified idraparinux sodium from a solution including the second mixture.

Figure 2:
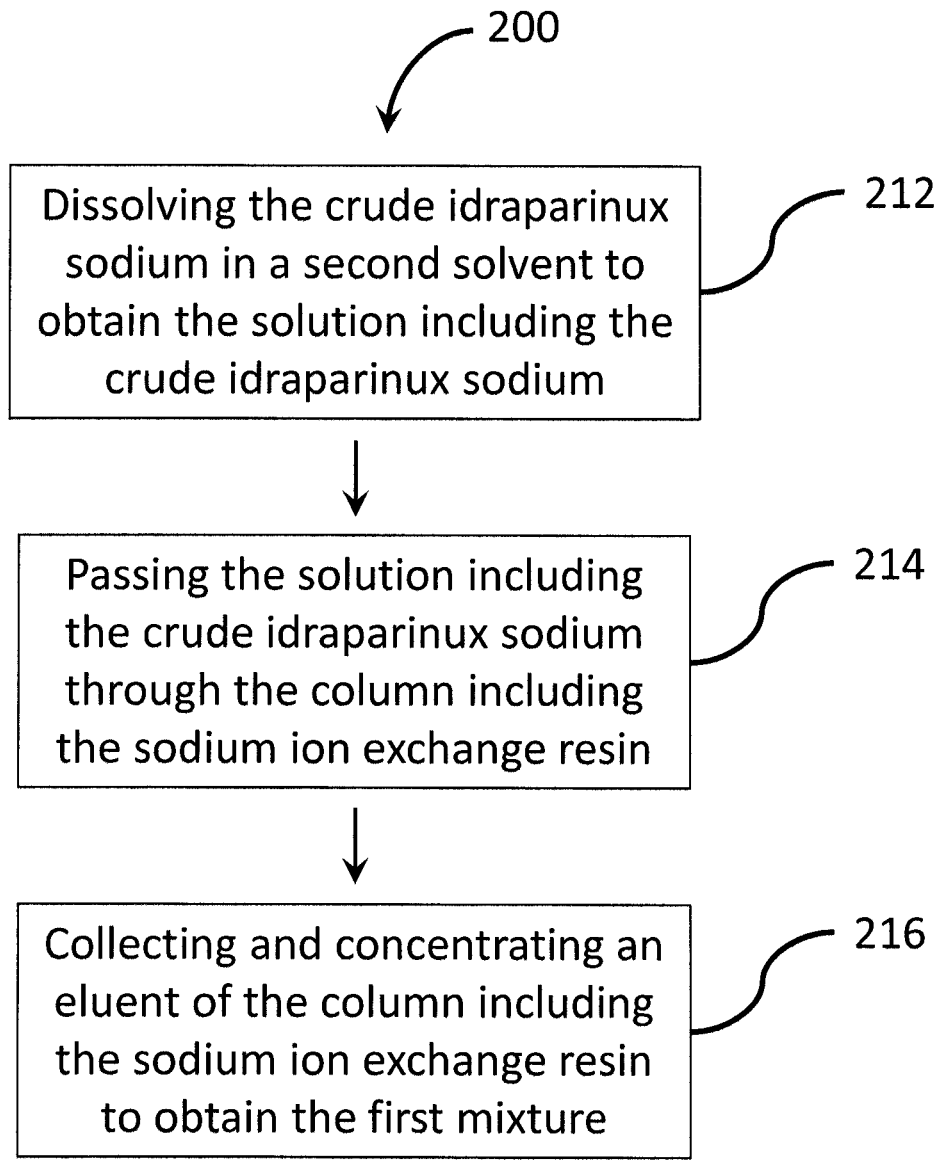
FIG. 2 is a flow chart showing a method for obtaining a first mixture according to an embodiment of the present disclosure.

The obtaining of the first mixture may further include dissolving the crude idraparinux in a solvent, and may further include collecting and concentrating an eluent of the sodium ion exchange resin. For example, FIG. 2 is a flow chart showing a method 200 for obtaining the first mixture according to an embodiment of the present disclosure. Referring to FIG. 2, the first mixture may be obtained by 212 dissolving the crude idraparinux sodium in a second solvent to obtain the solution including the crude idraparinux sodium; 214 passing the solution including the crude idraparinux sodium through the column including the sodium ion exchange resin; and 216 collecting and concentrating an eluent of the column including the sodium ion exchange resin to obtain the first mixture. For example, the concentrating of the eluent may include increasing a concentration of the first mixture (e.g., increasing a concentration of idraparinux sodium) in the eluent. As used herein, the term "eluent" refers to a solution that elutes from a column, and, depending on the context, the eluent may include a solvent (e.g., the second solvent), the first mixture, the second mixture, and/or an impurity. Additionally, in FIGS. 1 and 2, the active acts 104 and 214 of the passing of the solution including the crude idraparinux sodium through the column including the sodium ion exchange resin may be the same.

The crude idraparinux sodium may be synthesized utilizing any suitable method available in the art. For example, the crude idraparinux sodium may be synthesized utilizing the above-referenced [3+2] synthetic strategy according to Herczeg (Herczeg Mihály, "Novel Syntheses of Idraparinux, the Anticoagulant Pentasaccharide with Indirect Selective Factor Xa Inhibitory Activity", *Tetrahedron,* 2013, 69(15): 3149-3158) and/or Yu (Yu B. and Chen C., "Efficient Synthesis of Idraparinux, the anticoagulant pentasaccharide", *Bioorganic & Medicinal Chemistry Letters,* 2009, 19(14): 3875-3879). In some embodiments, the crude idraparinux sodium may have a purity of 60% to 70%, based on the total weight of the sample including the crude idraparinux sodium. The sample including the crude idraparinux sodium may include organic and inorganic impurities, such as organic impurities (e.g., carboxyl group containing and sulfonic group containing salts, such as disaccharide and trisaccharide isomers, triethylamine salt), and other inorganic impurities (e.g., sodium acetate, sulfate salt).

The second solvent may include any suitable solvent. For example, the second solvent may include water. The concentration of the crude idraparinux sodium in the second solvent may be about 0.1 to about 2.0 g/ml, for example, about 0.3 to about 0.8 g/ml.

The column including the sodium ion exchange resin may be a column in any suitable ion exchange chromatography instrument and the column may include any suitable sodium ion exchange resin. The column including the sodium ion exchange resin may include a Mono S 5/50 GL column or a Mono S 10/100 GL column, each of which is available from GE Healthcare Life Sciences, Little Chalfont, Buckinghamshire, UK, or the column may be filled by hand to include a Dowex 50WX8, 100-200 mesh, ion-exchange resin, or a Dowex Monosphere 88 resin, each of which is available from DOW Chemical Company, Michigan, USA. The mesh number of the column of sodium ion exchange resin may be 100 mesh to 200 mesh.

The method may further include washing the column including the sodium ion exchange resin with a third solvent during the collecting of the eluent of the column. The third solvent may include any suitable solvent. For example, the third solvent may include water (e.g., de-ionized water). The amount of the water utilized for washing the column including the sodium ion exchange resin may be 1 to 6 column volume, for example, about 1 to 3 column volume.

The collecting of the eluent may include collecting the eluent fraction by fraction (e.g., segment by segment) as it elutes from the column including the sodium ion exchange resin. The fractions of the eluent may be collected utilizing a fraction collector, for example, ÄKTA purifier 100, available from GE Healthcare Life Sciences, Little Chalfont, Buckinghamshire, UK. The fraction collector may utilize conductivity detection.

According to embodiments of the present disclosure, the eluent collected includes the idraparinux sodium in the sodium form. The carboxyl group and sulfonic group containing salts that are present as impurities in the sample including the crude idraparinux sodium are converted to sodium salts by the column including the sodium ion exchange resin as may be confirmed by an ion chromatography spectrometer.

The collected eluent may be concentrated using any suitable method to obtain the first mixture, (e.g., a mixture including idraparinux sodium) that has been purified by the sodium ion exchange resin. For example, the concentration of the first mixture (e.g., the concentration of the idraparinux sodium) in the collected eluent may be increased by utilizing vacuum drying, heating, or a combination thereof. The collected eluent may be concentrated at a temperature of about 20° C. to about 60° C., for example, about 30° C. to about 50° C. The vacuum may be about −0.05 MPa to −0.1 MPa, for example, about −0.07 MPa to −0.09 MPa. The first mixture (e.g., the mixture including the idraparinux sodium) obtained in this process may be a white solid or a light yellowish solid.

Figure 3:
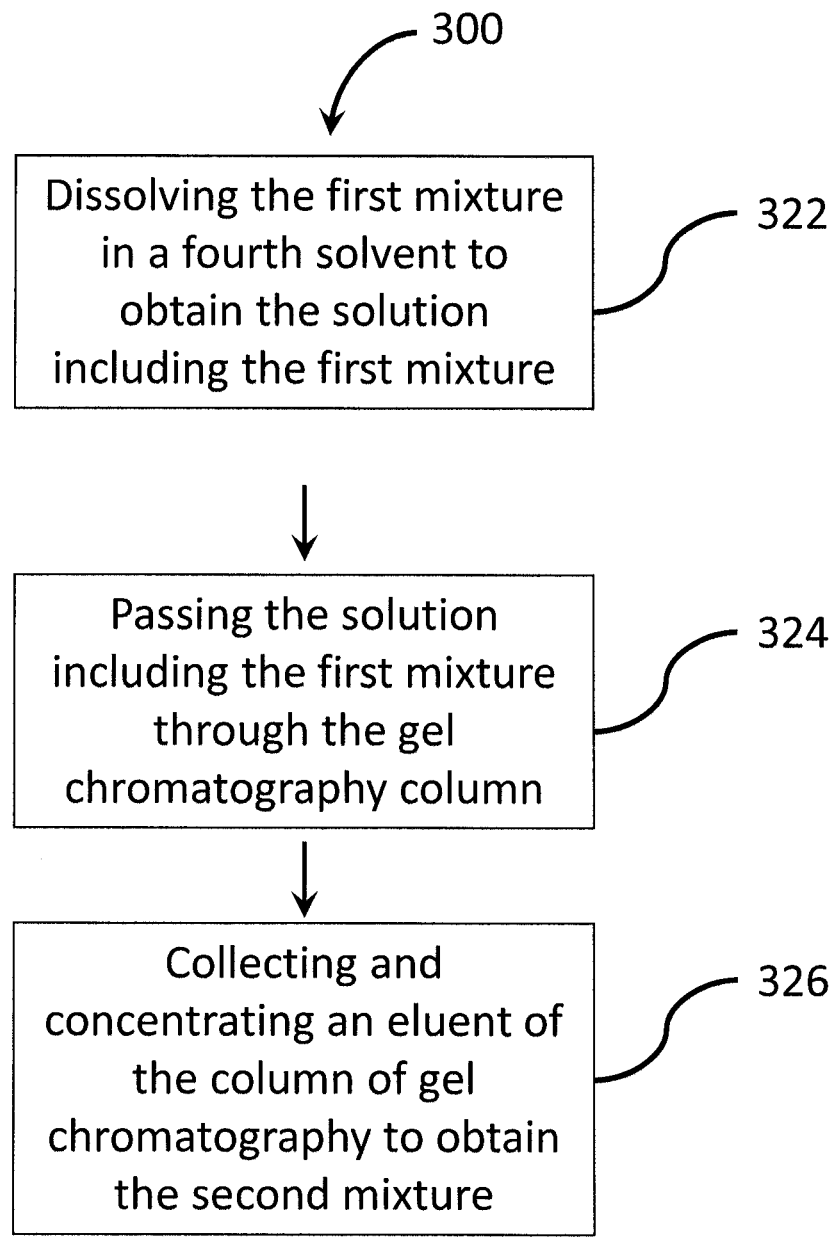
FIG. 3 is a flow chart showing a method for obtaining a second mixture according to an embodiment of the present disclosure.

The passing of the solution including the first mixture through a gel chromatography column to obtain the second mixture may further include dissolving the first mixture in a solvent (e.g., a fourth solvent), and may further include collecting and concentrating an eluent of the gel chromatography column. For example, FIG. 3 is a flow chart showing 300 a method for obtaining a second mixture according to an embodiment of the present disclosure. Referring to FIG. 3, the passing of the solution including the first mixture through the gel chromatography column may include: 322 dissolving the first mixture in a fourth solvent to obtain the solution including the first mixture; 324 passing the solution including the first mixture through the gel chromatography column; and 326 collecting and concentrating an eluent of the gel chromatography column to obtain the second mixture. In FIGS. 1 and 3, the active acts 104 and 324 of the passing of the solution including the first mixture through the gel chromatography column may be the same.

The fourth solvent may include a mixture of the first solvent and the second solvent, for example, a methanol-water mixture. The amount of the first solvent in the fourth solvent may be 0 v/v % to 10 v/v % (greater than 0 v/v % to 10 v/v %, or 2 v/v % to 10 v/v %) based on the total volume of the fourth solvent. For example, the amount of the first solvent in the fourth solvent may be 4 v/v % to 6 v/v % based on the total volume of the fourth solvent.

The concentration of the first mixture (e.g., the concentration of the idraparinux sodium) in the solution including the first mixture may be about 0.1 to about 2.0 g/ml, for example, about 0.3 to about 0.8 g/ml.

The gel chromatography column may include any suitable gel materials. For example, the gel chromatography column may include a beaded gel filtration medium prepared by cross-linking dextran with epichlorohydrin under alkaline conditions. Commercial examples of such gel materials may include glucan gels such as Sephadex G-10, G-15, G-25, or G-50, available from GE Healthcare Life Sciences, Little Chalfont, Buckinghamshire, UK.

The eluent of the gel chromatography column may include idraparinux sodium in a methanol-water mixture including 0 v/v % to 10 v/v % (e.g., greater than 0 v/v % to 10 v/v %, 2 v/v % to 10 v/v %, or 4 v/v % to 6 v/v %) of methanol, based on the total volume of the eluent.

According to embodiments of the present disclosure, salts having lower molecular weight (e.g., a molecular weight of less than 1200 g/mol), such as organic and/or inorganic salts including a carboxyl group and/or a sulfonic group may be removed as a result of the purification utilizing the gel chromatography column. When the eluent of the gel chromatography column still contains a substantial or significant amount of impurities (e.g., the salts), the eluent may be treated by passing it through the gel chromatography column a plurality of times until idraparinux sodium having a suitable purity (e.g., a purity of 99.0% based on the total weight of the sample including the idraparinux sodium) is obtained. According to other embodiments of the present disclosure, a plurality of gel chromatography columns may be utilized sequentially to effectively purify the solution containing the first mixture.

The concentrating of the eluent of the gel chromatography column to obtain the second mixture may be substantially similar to that disclosed above with respect to the first mixture.

Figure 4:
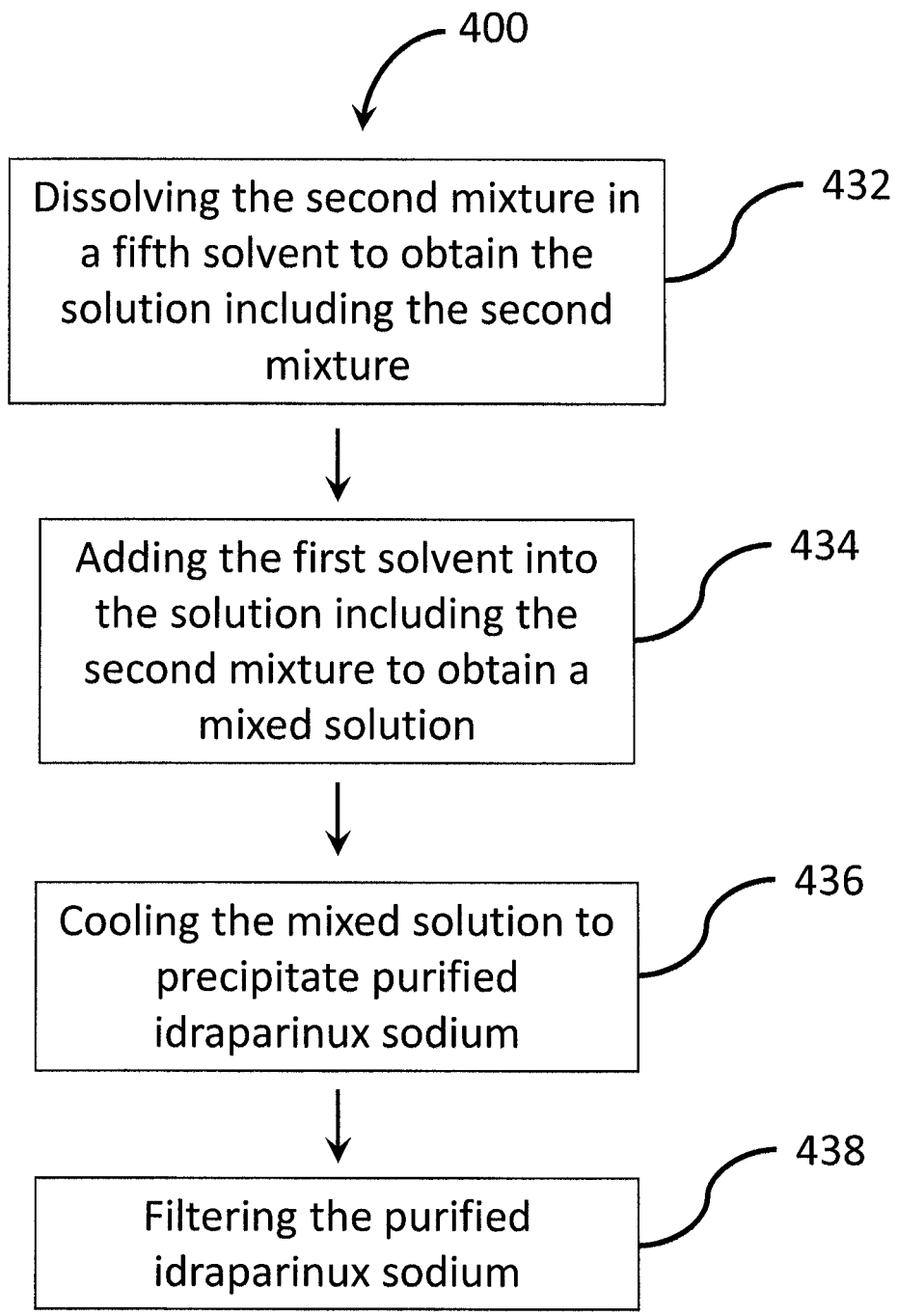
FIG. 4 is a flow chart showing a method for obtaining a purified idraparinux sodium according to an embodiment of the present disclosure.

Embodiments of the precipitating of the purified idraparinux sodium from a solution including the second mixture may further include the active acts shown in the flow chart of FIG. 4. Referring to FIG. 4, 400 the precipitating of the purified idraparinux sodium from the solution including the second mixture may include: 432 dissolving the second mixture in a fifth solvent to obtain the solution including the second mixture; 434 adding the first solvent into the solution including the second mixture to obtain a mixed solution; 436 cooling the mixed solution to precipitate purified idraparinux sodium, and 438 filtering the purified idraparinux sodium.

The concentration of the second mixture (e.g., the concentration of the idraparinux sodium) in the solution including the second mixture may be about 0.1 to about 2.0 g/ml, for example, about 0.4 to about 0.8 g/ml. The dissolving of the second mixture in the fifth solvent may be conducted at a temperature of about 30° C. to about 50° C. The mixed solution may be cooled to a temperature of about −30° C. to about 15° C. (e.g., about 10° C. to about 15° C.).

The first solvent utilized for the precipitating of the purified idraparinux sodium may include an alcohol, a ketone, acetonitrile, or a mixture thereof. The first solvent may be added slowly (e.g., dropwise) to the solution including the purified idraparinux sodium.

The first solvent may include an alcohol selected from methanol, ethanol, propanol, ethanediol, 1,2-propanediol, 1,3-propanediol, glycerine, and the like, and mixtures thereof.

The first solvent may include a ketone selected from acetone, butanone, and the like, and mixtures thereof.

A ratio of a volume of the first solvent to a volume of the fifth solvent may be about 1:1 to about 12:1, for example, about 2:1 to about 6:1.

The cooling of the mixed solution to a temperature of about −30° C. to about 15° C. (e.g., about 10° C. to about 15° C.) may be conducted with a slow cooling rate, for example, at about 5° C./min or less (e.g., about 0.2° C./min to about 5° C./min, or about 1° C./min to about 5° C./min).

As a result of the cooling of the mixed solution, idraparinux sodium is precipitated from the mixed solution. The precipitated idraparinux sodium may then be collected by filtration, washing, and drying to obtain the purified idraparinux sodium as a white solid.

According to embodiments of the present disclosure, the impurities remaining after the purification utilizing the column including the sodium ion exchange resin and the gel chromatography column, e.g., triethylamine salt carried over from the previous preparation steps, may be removed from the idraparinux sodium utilizing this additional purification step. The idraparinux sodium prepared according to the above embodiments may have a purity of greater than 90%, for example, greater than 95%, at least 99.0%, or greater than 99%.

Hereinafter, certain embodiments of the present disclosure will be described with reference to some examples. It should be understood that these examples are provided for illustration purposes only and are not to be construed in any way as limiting the present invention.

Example 1

20 g of crude idraparinux sodium synthesized utilizing the [3+2] synthesis strategy and having a purity of 60 to 70% was dissolved in 50 ml of de-ionized water to obtain a solution including crude idraparinux sodium. The solution was injected into a sodium ion exchange resin column. The column may include a Mono S 5/50 GL column or a Mono S 10/100 GL column, each of which is available from GE Healthcare Life Sciences, Little Chalfont, Buckinghamshire, UK, or the column may be filled by hand to include a Dowex 50WX8, 100-200 mesh, ion-exchange resin, or a Dowex Monosphere 88 resin, each of which is available from DOW Chemical Company, Michigan, USA. De-ionized water was utilized to wash the column. The amount of water utilized to wash the column may be 1 to 6 column volume, for example about 1 to 3 column volume. Fraction by fraction (segment by segment), the washed eluent solution was collected. That is, successive fractions of the eluent solution were collected as they eluted from the sodium exchange resin column. The collected eluent was then dried under vacuum to obtain 19.5 g of the first mixture (sodium ion exchange resin purified idraparinux sodium) as a white solid.

The first mixture was dissolved in 50 ml of 6 v/v % MeOH/H$_2$O to obtain a solution. The solution was injected into a gel chromatography column (Sephadex G-25, available from GE Healthcare Life Sciences, Little Chalfont, Buckinghamshire, UK). The column was washed with 6 v/v % MeOH/H$_2$O. The amount of MeOH/H$_2$O utilized to wash the column may be 1 to 12 column volume, for example, about 4 to 8 column volume. Fraction by fraction (segment by segment), the washed eluent solution was collected. That is, successive fractions of the washed eluent were collected as they eluted from the gel chromatography column. The collected eluent was then dried under vacuum to obtain 16.0 g of the second mixture (gel chromatography column purified idraparinux sodium) as a white solid.

The second mixture was dissolved in 40 ml of de-ionized water at 30° C. to obtain a solution. 400 ml of absolute ethanol (200 proof ethanol) was slowly added drop by drop to the solution while stirring to obtain a mixed solution. The mixed solution was cooled gradually to 15° C. over a time period of 3 hours. A white solid began to precipitate from the solution during the cooling to 15° C. After 1 hour of continuous stirring at 15° C., the precipitated solid was filtrated and dried at 40° C. in a vacuum dryer. 10.0 g of the purified idraparinux sodium was obtained as a white solid. The purity of idraparinux sodium in the white solid was 99.6% (based on the total peak area of the white solid) as measured by High Performance Liquid Chromatography (HPLC).

Example 2

40 g of crude idraparinux sodium synthesized utilizing the [3+2] synthesis strategy and having a purity of 60 to 70% was dissolved in 50 ml of de-ionized water to obtain a solution including crude idraparinux sodium. The solution was then injected into a sodium ion exchange resin column. The column including the sodium ion exchange resin may include a Mono S 5/50 GL column or a Mono S 10/100 GL column, each of which is available from GE Healthcare Life Sciences, Little Chalfont, Buckinghamshire, UK, or the column may be filled by hand to include a Dowex 50WX8, 100-200 mesh, ion-exchange resin, or a Dowex Monosphere 88, each of which is available from DOW Chemical Company, Michigan, USA. The column was washed with de-ionized water. The amount of water utilized to wash the column may be 1 to 6 column volume, for example about 1 to 3 column volume. Fraction by fraction (segment by segment), the washed eluent solution was collected. That is, successive fractions of the eluent solution were collected as they eluted from the sodium ion exchange resin column. The collected eluent was then dried under vacuum to obtain 38.0 g of the first mixture (sodium ion exchange resin purified idraparinux sodium) as a white solid.

The first mixture was dissolved in 50 ml of 4 v/v % MeOH/H$_2$O to obtain a solution. The solution was injected into a gel chromatography column (Sephadex G-50, available from GE Healthcare Life Sciences, Little Chalfont, Buckinghamshire, UK)). The column was washed with 6 v/v % MeOH/H$_2$O. The amount of MeOH/H$_2$O utilized to wash the column may be 1 to 12 column volume, for example, about 4 to 8 column volume. Fraction by fraction (segment by segment), the eluent solution was collected. That is, successive fractions of the washed eluent were collected as they eluted from the gel chromatography column. The collected eluent was then dried under vacuum to obtain 30.0 g of the second mixture (gel chromatography purified idraparinux sodium) as a white solid.

The second mixture was dissolved in 40 ml of de-ionized water at 30° C. to obtain a solution. 400 ml of a mixed solvent including ethanol and acetone (at a 1 to 1 volume ratio) was slowly added drop by drop to the solution while stirring to obtain a mixed solution. The mixed solution was cooled to 15° C. over a time period of 3 hours. A white solid began to precipitate from the solution during the cooling to 15° C. After 1 hour of continuous stirring at 15° C., the precipitated solid was filtrated and dried at 40° C. in a vacuum dryer. 25.0 g of the purified idraparinux sodium was obtained as a white solid. The purity of idraparinux sodium in the white solid was 99.5% (based on the total peak area of the white solid) as measured by HPLC.

Example 3

10 g of the crude idraparinux sodium synthesized utilizing the [3+2] synthesis strategy and having a purity of 60 to 70% was dissolved in 25 ml of de-ionized water to obtain a solution including crude idraparinux sodium. The solution was injected into a sodium ion exchange resin column. The column including the sodium ion exchange resin may include a Mono S 5/50 GL column or a Mono S 10/100 GL column, each of which is available from GE Healthcare Life Sciences, Little Chalfont, Buckinghamshire, UK, or the column may be filled by hand to include a Dowex 50WX8, 100-200 mesh, ion-exchange resin, or a Dowex Monosphere 88 resin, each of which is available from DOW Chemical Company, Michigan, USA. The column was washed with de-ionized water. The amount of water utilized to wash the column may be 1 to 6 column volume, for example about 1 to 3 column volume. Fraction by fraction (segment by segment), the washed eluent solution was collected. That is, successive fractions of the eluent solution were collected as they eluted from the sodium ion exchange resin column. The collected eluent was then dried under vacuum to obtain 9.5 g of the first mixture (sodium ion exchange resin purified idraparinux sodium) as a white solid.

The first mixture was dissolved in 25 ml of 7 v/v % MeOH/$H_2O$ to obtain a solution. The solution was injected into a gel chromatography column (Sephadex G-15, available from GE Healthcare Life Sciences, Little Chalfont, Buckinghamshire, UK). The column was washed with 6 v/v % MeOH/$H_2O$. The amount of MeOH/$H_2O$ utilized to wash the column may be 1 to 12 column volume, for example, about 4 to 8 column volume. Fraction by fraction (segment by segment), the sample eluent solution was collected. That is, successive fractions of the washed eluent were collected as they eluted from the gel chromatography column. The collected eluent was then dried under vacuum to obtain 8.0 g of the second mixture (gel chromatography purified idraparinux sodium) as a white solid.

The second mixture was dissolved in 25 ml of de-ionized water at 30° C. to obtain a solution. 250 ml of acetone was slowly added drop by drop to the solution while stirring to obtain a mixed solution. The mixed solution was cooled to 15° C. over a time period of 3 hours. A white solid began to precipitate from the solution during the cooling to 15° C. After 1 hour of continuous stirring at 15° C., the precipitated solid was filtrated and dried at 40° C. in a vacuum dryer. 6.0 g of the purified idraparinux sodium was obtained as a white solid. The purity of idraparinux sodium in the white solid was 99.6% (based on the total peak area of the white solid) as measured by HPLC.

While certain exemplary embodiments of the present disclosure have been illustrated and described, those of ordinary skill in the art will understand that various modifications, changes, alterations, and equivalent embodiments can be made without departing from the spirit and scope of the invention, as described in the following claims, and equivalents thereof.

What is claimed is:

1. A method for obtaining at least 99.0% pure idraparinux sodium comprising nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-idopyranuronosyl-(1→4)-2,3,6-tri-O-sulfonato-α-D-glucopyranoside, the method consisting of:
passing a solution comprising a crude idraparinux sodium through a column comprising a sodium ion exchange resin to obtain a first mixture;
passing a solution comprising the first mixture through a gel chromatography column to obtain a second mixture; and
precipitating the at least 99.0% pure idraparinux sodium at a temperature of about −30° C. to about 15° C. from a solution comprising the second mixture by dissolving the second mixture in a fifth solvent comprising water to obtain the solution comprising the second mixture and adding a first solvent to the solution comprising the second mixture to obtain a mixed solution,
wherein a ratio of a volume of the first solvent to a volume of the water of the fifth solvent is about 6:1 to about 12:1.

2. The method of claim 1, wherein the passing of the solution comprising the crude idraparinux sodium through the column comprising the sodium ion exchange resin comprises:
dissolving the crude idraparinux sodium in a second solvent to obtain the solution comprising the crude idraparinux sodium,
passing the solution comprising the crude idraparinux sodium through the column comprising the sodium ion exchange resin, and
collecting and concentrating an eluent of the column comprising the sodium ion exchange resin to obtain the first mixture.

3. The method of claim 2, wherein the second solvent comprises water.

4. The method of claim 2, wherein a concentration of the crude idraparinux sodium in the second solvent is about 0.1 to about 2.0 g/ml.

5. The method of claim 2, further comprising washing the column comprising the sodium ion exchange resin with a third solvent during the collecting of the eluent.

6. The method of claim 5, wherein the third solvent comprises water.

7. The method of claim 1, wherein a mesh number of the column comprising the sodium ion exchange resin is about 100 mesh to about 200 mesh.

8. The method of claim 1, wherein the gel chromatography column comprises a beaded gel filtration medium prepared by cross-linking dextran with epichlorohydrin under alkaline conditions.

9. The method of claim 5, wherein the passing of the solution comprising the first mixture through the gel chromatography column comprises:
dissolving the first mixture in a fourth solvent to obtain the solution comprising the first mixture,
passing the solution comprising the first mixture through the gel chromatography column, and
collecting and concentrating an eluent of the gel chromatography column to obtain the second mixture.

10. The method of claim 9, wherein the fourth solvent comprises a mixture of the third solvent and the second solvent.

11. The method of claim 10, wherein the amount of the third solvent in the fourth solvent is 0 v/v % to 10 v/v % based on a total volume of the fourth solvent.

12. The method of claim 10, wherein the amount of the third solvent in the fourth solvent is 4 v/v % to 6 v/v % based on a total volume of the fourth solvent.

13. The method of claim 9, wherein a concentration of the first mixture in the solution comprising the first mixture is about 0.1 to about 2.0 g/ml.

14. The method of claim 9, wherein the passing of the solution comprising the first mixture through the gel chromatography column is conducted a plurality of times.

15. The method of claim 9, wherein the eluent of the gel chromatography column comprises a methanol-water mixture comprising 0 v/v % to 10 v/v % of methanol based on a total volume of the eluent.

16. The method of claim 9, wherein the eluent of the gel chromatography column comprises a methanol-water mixture comprising 4 v/v % to 6 v/v % of methanol based on a total volume of the eluent.

17. The method of claim 1, wherein the first solvent utilized for the precipitating of the at least 99.0% pure idraparinux sodium comprises an alcohol, a ketone, acetonitrile, or a mixture thereof.

18. The method of claim 17, wherein the alcohol is selected from the group consisting of methanol, ethanol, propanol, ethanediol, 1,2-propanediol, 1,3-propanediol, glycerine, and mixtures thereof.

19. The method of claim 17, wherein the ketone is selected from the group consisting of acetone, butanone, and mixtures thereof.

20. The method of claim 1, wherein the precipitating of the at least 99.0% pure idraparinux sodium from the solution comprising the second mixture further comprises:
cooling the mixed solution to precipitate the at least 99.0% pure idraparinux sodium, and
filtering and collecting the at least 99.0% pure idraparinux sodium.

21. The method of claim 20, wherein a concentration of the second mixture in the solution comprising the second mixture is about 0.1 to about 2.0 g/ml.

22. The method of claim 20, wherein the dissolving of the second mixture in the fifth solvent is conducted at a temperature of about 30° C. to about 50° C.

23. The method of claim 20, wherein the mixed solution is cooled to a temperature of about −30° C. to about 15° C.

24. The method of claim 20, wherein a ratio of a volume of the first solvent to a volume of the fifth solvent is about 8:1 to about 10:1.

25. A method for obtaining at least 99.0% pure idraparinux sodium comprising nonasodium methyl 2,3,4-tri-O-methyl-6-O-sulfonato-α-D-glucopyranosyl-(1→4)-2,3-di-O-methyl-β-D-glucopyranuronosyl-(1→4)-2,3,6-tri-O-sulfonato-α-D-glucopyranosyl-(1→4)-2,3-di-O-methyl-α-L-idopyranuronosyl-(1→4)-2,3,6-tri-O-sulfonato-α-D-glucopyranoside, the method consisting of:
passing a solution comprising a crude idraparinux sodium and a first solvent through a gel chromatography column to obtain a first mixture;
passing a solution comprising the first mixture and a second solvent through a column comprising a sodium ion exchange resin to obtain a second mixture; and
precipitating the at least 99.0% pure idraparinux sodium at a temperature of about −30° C. to about 15° C. from a solution comprising the second mixture by dissolving the second mixture in a third solvent comprising water to obtain the solution comprising the second mixture and adding a fourth solvent to the solution comprising the second mixture to obtain a mixed solution,
wherein a ratio of a volume of the fourth solvent to a volume of the water of the third solvent is about 6:1 to about 12:1.

* * * * *